United States Patent
Kononyuk et al.

(10) Patent No.: US 11,330,072 B2
(45) Date of Patent: May 10, 2022

(54) DEVICE AND METHOD FOR LABORATORY DATA DISTRIBUTION

(71) Applicant: TECHNO-PATH MANUFACTURING LIMITED, Tipperary (IE)

(72) Inventors: Yuriy Kononyuk, Tipperary (IE); Ger Kennedy, Tipperary (IE); Ed MacMahon, Tipperary (IE)

(73) Assignee: TECHNO-PATH MANUFACTURING LIMITED

( * ) Notice: Subject to any disclaimer, the term of this patent is extended or adjusted under 35 U.S.C. 154(b) by 0 days.

(21) Appl. No.: 16/969,448

(22) PCT Filed: Feb. 12, 2019

(86) PCT No.: PCT/EP2019/053465
§ 371 (c)(1),
(2) Date: Aug. 12, 2020

(87) PCT Pub. No.: WO2019/155093
PCT Pub. Date: Aug. 15, 2019

(65) Prior Publication Data
US 2020/0374359 A1    Nov. 26, 2020

(30) Foreign Application Priority Data
Feb. 12, 2018 (EP) .................................. 18156379

(51) Int. Cl.
*G06F 15/16* (2006.01)
*H04L 67/565* (2022.01)
(Continued)

(52) U.S. Cl.
CPC ........ *H04L 67/2823* (2013.01); *G06F 16/258* (2019.01); *G16H 10/40* (2018.01);
(Continued)

(58) Field of Classification Search
None
See application file for complete search history.

(56) References Cited

U.S. PATENT DOCUMENTS

2005/0060202 A1    3/2005  Taylor
2006/0222003 A1    10/2006 Majumdar
(Continued)

*Primary Examiner* — Brian Whipple
*Assistant Examiner* — Gregory P Tolchinsky
(74) *Attorney, Agent, or Firm* — Clark Hill PLC; James R. Foley

(57) ABSTRACT

A networked data capturing device is provided, which implements a method of automatically distributing test data output by a laboratory equipment device, wherein the test data is representative of testing performed by the laboratory equipment device and formatted according to an application layer protocol, across a network. The networked data capturing device comprises networking means for connecting to one or more emote servers over networks, a local data input interface for connecting to the laboratory equipment device, and is configured to listen for and automatically obtain the test data through the local data input interface, to process the obtained data into an alternative format according to a remote parameterisation of the device, and to automatically communicate the processed data to at least one remote server with the networking means.

19 Claims, 7 Drawing Sheets

(51) Int. Cl.
*G16H 10/40* (2018.01)
*G16H 40/40* (2018.01)
*G06F 16/25* (2019.01)
*H04L 67/12* (2022.01)
*H04L 69/08* (2022.01)

(52) U.S. Cl.
CPC ............ *G16H 40/40* (2018.01); *H04L 67/12* (2013.01); *H04L 69/08* (2013.01)

(56) References Cited

U.S. PATENT DOCUMENTS

| | | | |
|---|---|---|---|
| 2010/0179819 A1* | 7/2010 | Herbst | G16H 10/60 705/2 |
| 2010/0299517 A1 | 11/2010 | Jukic et al. | |
| 2013/0045685 A1* | 2/2013 | Kiani | G08B 21/24 455/41.2 |
| 2015/0097701 A1* | 4/2015 | Al-Ali | G06F 21/84 340/870.07 |
| 2017/0287093 A1* | 10/2017 | Tochilnik | G06F 16/116 |
| 2017/0324606 A1 | 11/2017 | Hobbs | |

\* cited by examiner

DEVICE AND METHOD FOR LABORATORY DATA DISTRIBUTION

FIELD

The present disclosure relates to a device for automating the distribution of data output by laboratory equipment, and to a corresponding method of distributing data.

BACKGROUND

Modern scientific and clinical concerns can include a wide variety of laboratory equipment devices acquired from a correspondingly-wide variety of manufacturers, spanning several generations of hardware interfaces and data computing formats and protocols.

It is accordingly common to find, in such environments, a heterogeneous mix of laboratory equipment devices accruing a similarly-heterogeneous suite of data output connectors, wherein some devices may comprise only serial data output connectors conforming to the Recommended Standard 232 ('RS-232') format; some more recent devices may also, or instead, comprise Universal Serial Bus ('USB') connectors and at least one 8 position 8 contact ('8P8C', 'also RJ45') connector for local and wide area network interfacing; and some other, still more recent, devices may comprise wireless network connectivity conforming to the Bluetooth® or Wi-Fi® networking standard.

It is also increasingly common to find laboratory information systems ('LIS') and/or laboratory information management system ('LIMS') implementing networks both for interconnecting such laboratory equipment devices with information management systems which, typically, host databases for storing test data output by the laboratory equipment and facilitating its analysis; and for integrating the set of diverse and disparate laboratory equipment devices as a data-coherent whole, to the extent permitted by legacy interfaces and data formats.

Efforts have been undertaken to standardise data formats, messages and communication protocols for facilitating such integrating. ASTM standard E1238 is one of the earliest standards in the field of clinical data transfers between independent computers, and is still in use for batch and reference laboratory interfaces. E1238 is technically aligned with a set of international standards promulgated by Health Level 7 ('HL7') International, and which focus on the application layer, being "layer" 7 in the Open Systems Interconnection ('OSI') model. HL7 standards are more recent standards than ASTM E1238, and are the most commonly used in the United States for numeric, textual, and coded clinical data, under which data messages are sent in an ASCII delimited format such as .txt or .csv or, according to more recent developments, in eXtended Markup Language ('XML') or JSANO or JSON formats.

Such normalisation efforts notwithstanding, the sheer volume of scientific and healthcare segments, procedures and data-producing equipment, maintains an inherently high degree of heterogeneity across laboratory data connections, file and data types, data messaging conventions and protocols, which is compounded by the device-independent character of LIS and LIMS and the pace of software and operating systems development of computers.

For example, whilst most laboratory equipment makers have long configured the firmware in laboratory devices for outputting test data in flat files of a generic format (such as the afore-mentioned .txt or .csv formats) and, in more recent times, designed such laboratory devices with local network connectivity to permit the exporting of flat files to a local network storage address, such as a shared file directory, the purchase of an instrument by a scientific or medical site rarely engages the equipment maker to customize the instrument connectivity and data transfer to accommodate that site's LIS parameters. Reciprocally, it is impractical for a LIS supplier to design and implement connectivity and data templates for every possible legacy, up to state-of-the-art, laboratory equipment.

Further, most modern computers now lack a serial-type data input port and, as their operating system is in constant need of updating for security patching and interoperability implementing, administrators of data networks and system in scientific and clinical concerns often introduce procedural barriers to the acquisition and subsequent sharing of laboratory data, for instance when the administrator stipulates permanent real-time anti-virus protection on computers, but the laboratory equipment maker or the LIS or LIMS supplier stipulates incompatibility of its equipment or software with real-time virus protection. Various systems have been proposed in published patent applications such as US2005/060202 (Taylor et al) and US2017/324606 (Hobbs et al).

However a number of problems with the above implementations is that connectivity solutions and data conversion procedures are frequently engineered ad hoc, invariably requiring additional computing resources to bridge connectivity data format and procedural incompatibilities, irrespective of where and how they arise. Notwithstanding the existence of simple solutions to bridge incompatible connectors, such as a conventional serial-to-USB adapter for example, known technologies all still appear to require a distinct computer terminal, bespoke software from the laboratory equipment vendor and/or the LIS supplier and user interaction with both, in order to acquire data from a laboratory equipment device and process it into a usable format, i.e. to extract the values, parameters and similar quantitative data corresponding to the actual sampling results output by the laboratory equipment.

Accordingly there is a long standing requirement for a solution, which should desirably remove any legacy requirement to process or otherwise reformat data output by laboratory equipment at a user-operated workstation.

SUMMARY

The present invention mitigates shortcomings associated with the prior art of reference by providing a networked set-and-forget device, adapted to obtain and automatically convert test data output by laboratory equipment and/or stored in a local file server, into a second data format, then automatically communicate the processed data to one or more remote servers across one or more networks.

According to an aspect of the present invention therefore, there is provided a networked data capturing device, comprising networking means for connecting to one or more remote servers over networks; at least one local data input interface for connecting to at least one laboratory equipment device; memory means storing computer executable instructions; and at least one processor configured to access the memory means and to execute the stored computer executable instructions to poll the at least one local data input interface for any data output by the at least one laboratory equipment device; automatically obtain output test data representative of testing performed by the laboratory equipment device and formatted according to an application layer protocol; automatically process the obtained data into an alternative format according to a remote parameterisation of the device; and automatically communicate the processed data to at least one remote server with the networking means.

Advantageously, the combination of software and hardware as the device of the invention automates both the capture of laboratory data from a variety of data protocols and, after its real-time processing for transforming it into a usable format, its downstream processing at remote network locations, usefully removing any requirement for manual intervention in the laboratory environment, thus removing any potential for communication delays, for processing delays and for introducing errors in the data or in communication procedures. It will be appreciated that the invention can collect data from a range of devices that carry out laboratory testing, process only the data as determined in the software driver contained on the device, evaluate that data against defined rules and limits, and alerts the user via a display on the device. In one embodiment if the data is good (for example the colour green) or bad (for example the colour red) can be easily displayed. The evaluation of the data can be performed in a standalone manner by the device or by learning and receiving data from a system connected via LAN or from the internet. Utilising the flexibility of IoT (internet of things) technology the device can work as a standalone entity for evaluating performance of the instrument or as a part of a system receiving information back on the data evaluation.

Additional advantages of the device is that the device can work independently to collect, transform, evaluate, and notify of good or bad data without the requirement for interaction with other systems. Through identifiers in the data stream, the device is configured to build up a history of data types and then select the data to process based on the identifiers it has collected and determined to be the relevant ones.

It will be further appreciated that the device can be scaled to work as part of an overall distributed IoT system by collecting, transforming, and submitting data to a centralised system which communicates information back to the device after evaluating the data and allows the end user to be notified by a visual identifier on the device as to the nature of the data (good or bad). In addition, the device combines hardware and software in one enclosure, removing the requirements for separate collection devices that must communicate with another software system to transform the data into usable format.

In an embodiment of the networked data capturing device, the at least one processor is configured to execute the stored computer executable instructions to obtain test data by intercepting a bit stream output by the at least one laboratory equipment device through the at least one local data input interface.

In a further or complementary embodiment of the networked data capturing device, the at least one processor is configured to execute the stored computer executable instructions to capture the data into a first-in-first-out buffer instantiated in memory for processing substantially in real-time by a translating module according to downloaded formatting parameters to automatically obtain the test data. Through identifiers contained in the data stream, the device is configured to build up a history of data types and then select the data to process based on the identifiers it has collected and determined to be the relevant ones.

In a further or complementary embodiment of the networked data capturing device, the at least one processor is configured to execute the stored computer executable instructions to alternatively obtain test data by loading test data from a laboratory information system (LIS) file server.

In a further or complementary embodiment of the networked data capturing device, the at least one remote server is one selected from the group comprising a client file server connected to a local area network, a database server connected to a local area network, a database server connected to a wide area network and a web server connected to a wide area network.

In a further or complementary embodiment of the networked data capturing device, the at least one local data input interface comprises a serial data input connector, or a Universal Serial Bus (USB) connector, or an 8 position 8 contact (8P8C) connector.

According to another aspect of the present invention, there is also provided a laboratory data distribution system comprising at least one laboratory equipment device having a local data output interface and adapted both to process one or more samples and to output sampling results as the test data through the local data output interface, and at least one networked data capturing device as described and/or claimed herein, having its at least one local data input interface connected to the local data output interface.

In an embodiment of the system, wherein the at least one laboratory equipment device is connected to a laboratory information system or laboratory information management system through the local data output interface, the connection between the at least one laboratory equipment device and the at least one networked data capturing device comprises a split connection passing test data through to the laboratory information system or laboratory information management system.

In a further or complementary embodiment of the system, the remote server hosts a database of test data.

Thus the system of the invention can effectively obtain data either as test data directly from laboratory equipment, or as file exports from middleware systems or laboratory information systems at a file server, process that obtained data to extract only relevant or pertinent portions thereof into a database-compatible format, and submit the processed data to another location such as a central database store or wide area network destination location. Embodiments of the system may further provide mapping capabilities, wherein a system user is able to specify a specific format into which the obtained data is processed onto the outgoing data stream.

According to a further aspect of the present invention, there is also provided a method of distributing test data output by at least one laboratory equipment device, the method comprising the steps of connecting at least one local data input interface of a networked data capturing device according to any of claims 1 to 6 to the at least one laboratory equipment device; polling the at least one local data input interface for data output by the at least one laboratory equipment device; automatically obtaining the test data, wherein the test data is representative of testing performed by the laboratory equipment device and formatted according to an application layer protocol; automatically processing the obtained data into an alternative format according to a remote parameterisation of the device; and automatically communicating the processed data to a remote server with the networking means.

In an embodiment of the method, the step of automatically obtaining the test data may comprise the further step of intercepting a bit stream output by the at least one laboratory equipment device through the at least one local data input interface, based upon a polling result; or the step of loading test data from a data file stored at a local file server connected to the network.

In a further or complementary embodiment of the method, the step of automatically processing the obtained data may comprise the further steps of registering the or each networked data capturing device to the at least one remote server, inputting and storing parameterisation of the device at the at least one remote server; and downloading the stored parameterisation with the or each networked data capturing device from the at least one remote server.

In a further or complementary embodiment of the method, the at least one remote server is preferably selected from the group comprising a client file server connected to a local area network, a database server connected to a local area network, a database server connected to a wide area network and a web server connected to a wide area network. A variant of this method may comprise the further step of loading a set of computer-readable instructions into the networked data capturing device from the database server or the web server over the wide area network for configuring the networked data capturing device to perform steps of the method according to the invention.

In one embodiment the step of automatically obtaining the test data comprises the step of capturing the data into a first-in-first-out buffer instantiated in memory for processing substantially in real-time by a translating module according to downloaded formatting parameters to automatically obtain the test data.

According to yet another aspect of the present invention, there is also provided non-transitory computer-readable medium storing computer-executable instructions that, when executed by at least one processor, configure the at least one processor to implement a method as described hereinabove and thus to perform operations comprising polling a local data input interface connected to a data output interface of at least one laboratory equipment device, for any data output by the at least one laboratory equipment device; automatically obtaining test data, wherein the test data is representative of testing performed by the laboratory equipment device and formatted according to an application layer protocol; automatically processing the obtained data into an alternative format according to a remote parameterisation of the device; and automatically communicating the processed data to a remote server with networking means.

In any of the device, system, method, computer-executable instructions and their various embodiments introduced hereinabove, the obtained test data is preferably formatted according to an application layer protocol compliant with a messaging format, for example the Health Level 7 messaging format.

Other aspects of the present invention are as stated in the appended claims.

BRIEF DESCRIPTION OF THE DRAWINGS

The invention will be more clearly understood from the following description of an embodiment thereof, given by way of example only, with reference to the accompanying drawings, in which:—

DETAILED DESCRIPTION OF THE DRAWINGS

There will now be described byway of example a specific mode contemplated by the inventors. In the following description numerous specific details are set forth in order to provide a thorough understanding. It will be apparent however, to one skilled in the art, that the present invention may be practiced without limitation to these specific details. In other instances, well known methods and structures have not been described in detail so as not to unnecessarily obscure the description.

Figure 1:
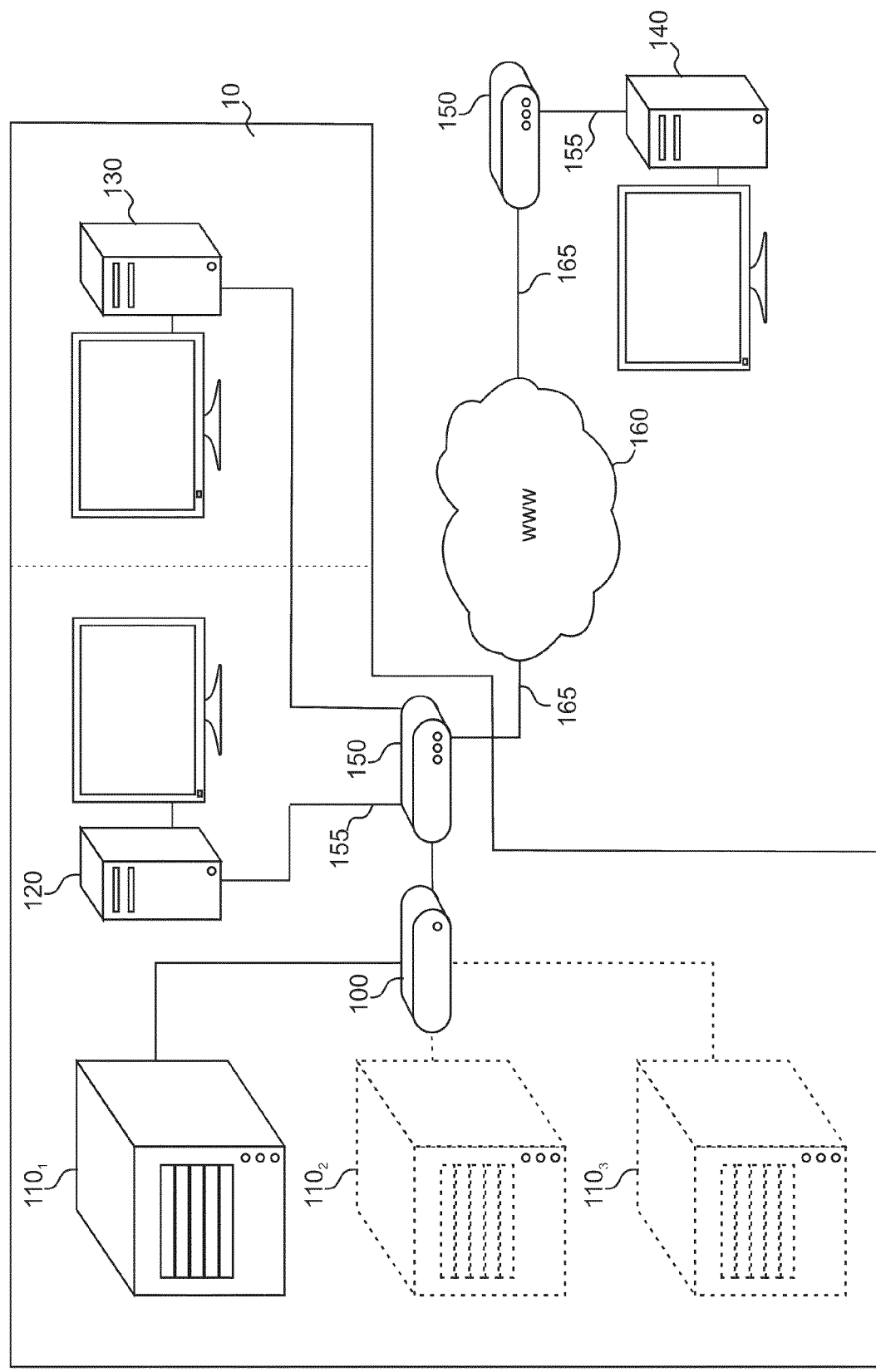
FIG. 1 illustrates a laboratory environment with a plurality of data processing devices and networks, including a networked data capturing device according to the invention, laboratory equipment devices, a user terminal and both local and remote servers.

Referring now to the figures and initially FIG. 1, there is shown a distributed data processing environment comprising a laboratory environment 10 having a plurality of data processing devices, including a networked data capturing device 100 according to an embodiment of the invention, laboratory equipment devices $110_{1,2,3}$, a user terminal 120 and a local LIS fileserver 130.

In the example, at least one laboratory equipment device 110$i$ is a device processing biological or chemical samples, which outputs sampling test data through a single RS232 port, such as a DB9 connector. The laboratory device 110$i$ is connected, through a compatible serial cable, to a serial or USB data input connector of the user terminal 120, respectively through a matching DB9 connector or via a USB socket configured with a serial-to-USB pass-through connector. It will be readily understood to the skilled person that the laboratory equipment device 110$i$ may be connected to the local LIS fileserver 130 instead of the user terminal 120, since either configuration corresponds to a conventional configuration and is immaterial to the inventive principle disclosed and described herein.

Each of the user terminal 120 and the local LIS fileserver 130 is a personal computer device, which emits and receives data encoded as digital signals over wired and/or wireless network messages, wherein such messages are routed by a router device 150 implementing a wired local area network ('LAN') 155 operating according to the IEEE 802.3-2008 Gigabit Ethernet transmission protocol, and optionally a high-bandwidth wireless local area network ('WLAN') operating according to the IEEE 802.11 Wi-Fi wireless transmission protocol. The router device 150 is itself also connected to a wide area network ('WAN') 160 via a conventional ADSL or optical fibre connection to a wired telecommunication network 165, wherein the router device 150 interfaces either the user terminal 120, or the local LIS fileserver 130, or both computers with the WAN 160.

A server 140 is also shown in FIG. 1 and which is remote from the laboratory environment 10, but which is likewise interfaced with the WAN 160 through a local router device 150 which implements its own LAN 155 and which is similarly connected to the WAN 160 via a conventional ADSL or optical fibre connection to a wired telecommunication network 165.

In the embodiment described, the networked data capturing device 100 is adapted to listen passively to the output test data streamed by the laboratory equipment device $110_1$ serial port, to automatically process any such output test data for extracting sampling values, parameters and similar other quantitative data from same, formatting same according to predefined parameters, and lastly to automatically forward the processed data to the remote server 140 across the WAN 160, including through any firewall device, apparatus or construct implemented by the router 150 in the laboratory environment 10.

Accordingly the networked data capturing device 100 is connected, firstly, to the single RS232 serial port of the laboratory equipment device $110_1$ with a Y-shaped splitter serial cable, having its single-side DB9 connection engaged with the serial port of the laboratory equipment device $110_1$, a first of its dual-side DB9 connectors engaged with a matching serial DB9 connector (or a USB socket configured with a serial-to-USB pass-through connector) of the networked data capturing device 100, and the second of its dual-side DB9 connectors engaged with the user terminal 120 or the local LIS fileserver 130: this configuration effectively duplicates the data signal output by the laboratory equipment device $110i$ and permits passive streaming of the test data to the networked data capturing device 100 without hindering the legacy connection.

It will be readily understood by the skilled person from the present disclosure, that the above configuration is provided by way of example only, and may be subject to many ad hoc changes depending on the connectivity hardware featured by laboratory equipment devices, on whether a laboratory equipment device requires any connection to a computer such as the user terminal 120 and/or the LIS fileserver 130 for its use, on whether such a connection can or cannot be passed through a third party device such as networked data capturing device 100, and more, without impacting the functionality of the networked data capturing device 100 and the inventive principles described herein in any way.

For purposes of automatically forwarding the processed data to the remote server 140 across the WAN 160, the networked data capturing device 100 is also connected, secondly, to the router 150 through the LAN 155 or WLAN, whereby network connectivity and interoperable networking protocols of each described data processing device 100, 120, 130, 140 allow the terminals to connect to one another and communicate data to and receive data from one another according to the methodology described herein. In that context, the router 150, or an associated firewall device if firewalling is not implemented by the router itself, is preferably configured to allow outbound network messaging from the networked data capturing device 100, i.e. network data addressed to the remote server 140, through one or two specific ports, for instance 80 and/or 443, to balance the conflicting requirements of permitting non-monitored communications by the networked data capturing device 100 to the remote server 140 outside the laboratory environment 10 and LAN 155, and of maintaining network and data security at the laboratory environment 10. The device can be set to communicate outbound on whatever port a user would like. An advantage of using ports 80 or 443 is that these are common ports that are usually open for communication outbound at most laboratories and this makes the device more user friendly and limits the requirement for user based intervention. The internet based server can listen for communication on port 80 or 443 which are standard ports used for internet communication.

Figure 2:
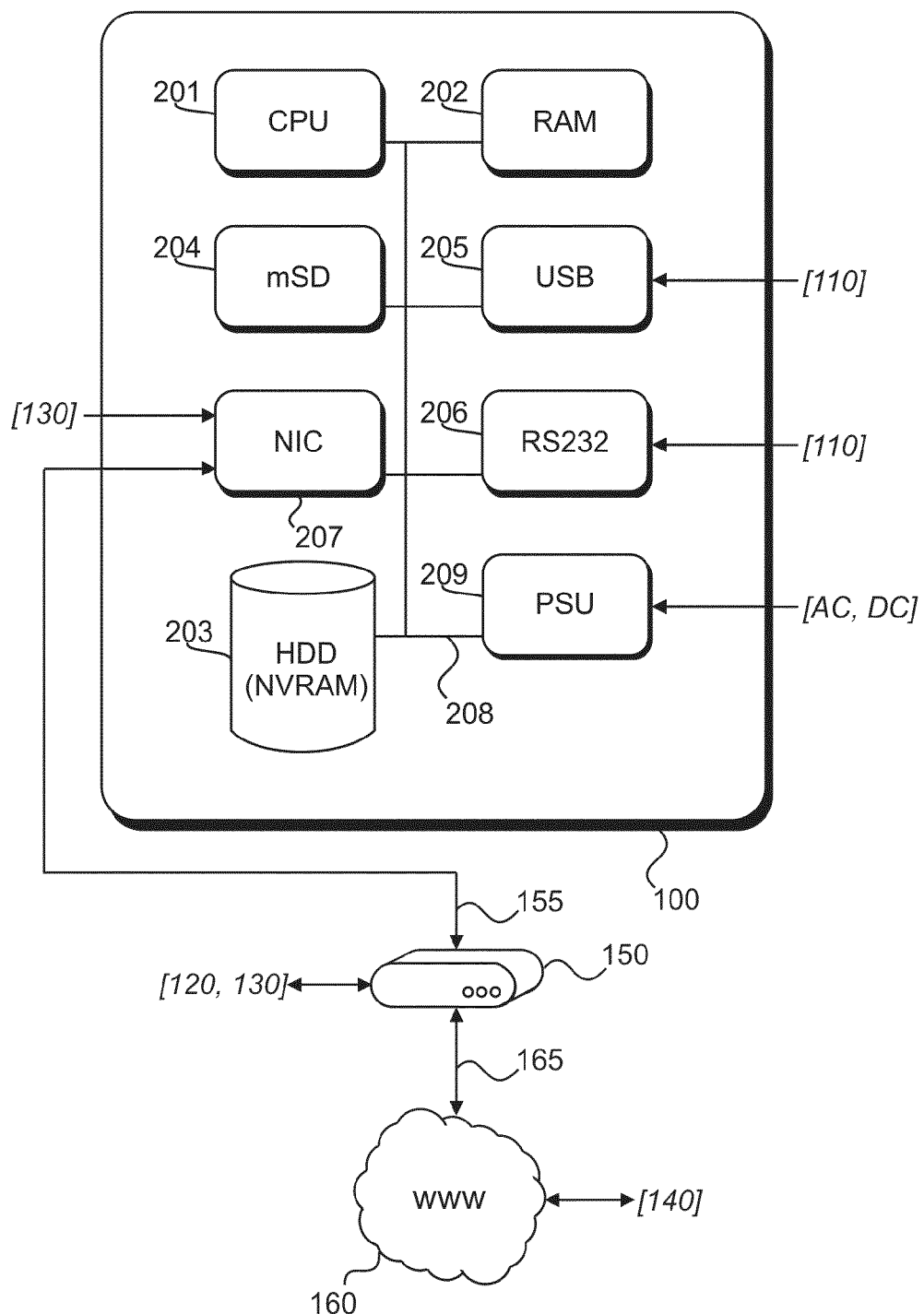
FIG. 2 shows a bloc diagram of an embodiment of the networked data capturing device of FIG. 1, including a memory, a processor, networking means and a data input interface.

FIG. 2 shows a bloc diagram of an embodiment of the networked data capturing device 100 of FIG. 1, in this example a single board computer device 100. The capturing device 100 accordingly includes a central data processing unit ('CPU') 201 such as a general-purpose microprocessor, for instance conforming to the Cortex™ architecture manufactured by ARM™, acting as the main controller of the capturing device 100 for providing task co-ordination and data processing functionality. Sets of instructions and data for the CPU 201 are stored in memory means, comprising of volatile random-access memory (RAM) 202 and/or non-volatile random-access memory (NVRAM) 203 and/or a combination thereof.

Embodiments of the capturing device 100 may further comprise a selectively removable memory means, shown in the example as a micro Secure Digital™ ('mSD') card reader-writer module 204, to facilitate ad hoc expansion of the data storage capacity of the capturing device 100 beyond the onboard RAM/NVRAM storage volume. Embodiments of the capturing device 100 may instead include only that selectively removable memory means 204 which, when containing a suitable flash memory storage medium (not shown), dispense with the requirement for onboard RAM 202 and/or NVRAM 203.

A universal serial bus (USB) input/output interface 205 facilitates connection to one or more laboratory equipment device(s) $110_N$, optionally with the adjunction of an external serial-to-USB interfacing adapter depending on the hardware connectivity format of the laboratory equipment device 110, and which permits the output test data stream to pass through to the user terminal 120 and/or LIS server 130 unimpeded when used in conjunction with a splitter cable as previously described. Embodiments of the capturing device 100 may also, or instead, comprise a legacy serial input/output interface 206, having substantially the same purposes and functionalities as the USB interface 205 and dispensing with the need for an external serial-to-USB interfacing adapter when the hardware connectivity format of the laboratory equipment device 110 is also of the serial type.

A wired network interface card (NIC) 207 provides the interface to the LAN network connection 155 with the router device 150, and all of the above-described components of the capturing device 100 are both connected to a data input/output bus 208, over which they communicate, and powered by a power supply unit 209, which receives electrical power from a local mains power source and transforms same according to component ratings and requirements. Accordingly, test data output by a laboratory equipment device 110 may be received from USB I/O interface 205 and/or serial I/O interface 206, stored in the memory means 202 or 203 or 207, processed by the CPU 201 according to a set of instructions also stored in the memory means 202 or 203 or 207, and the processed data communicated to the remote server 140 through the NIC 207.

Figure 3:
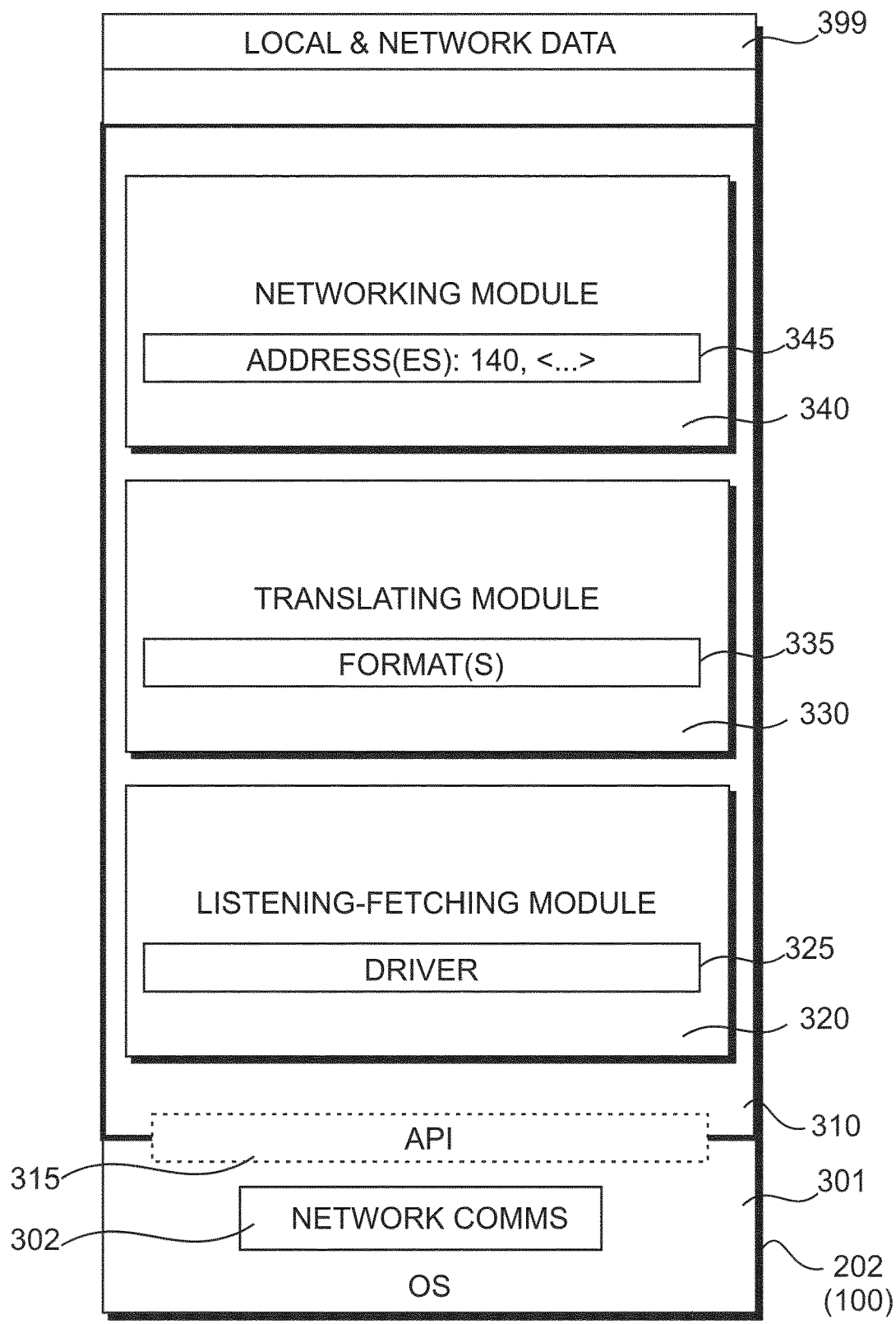
FIG. 3 represents the contents of the memory of FIG. 2 at runtime, including an operating system, a set of instructions and discrete data modules thereof.
Figure 4:
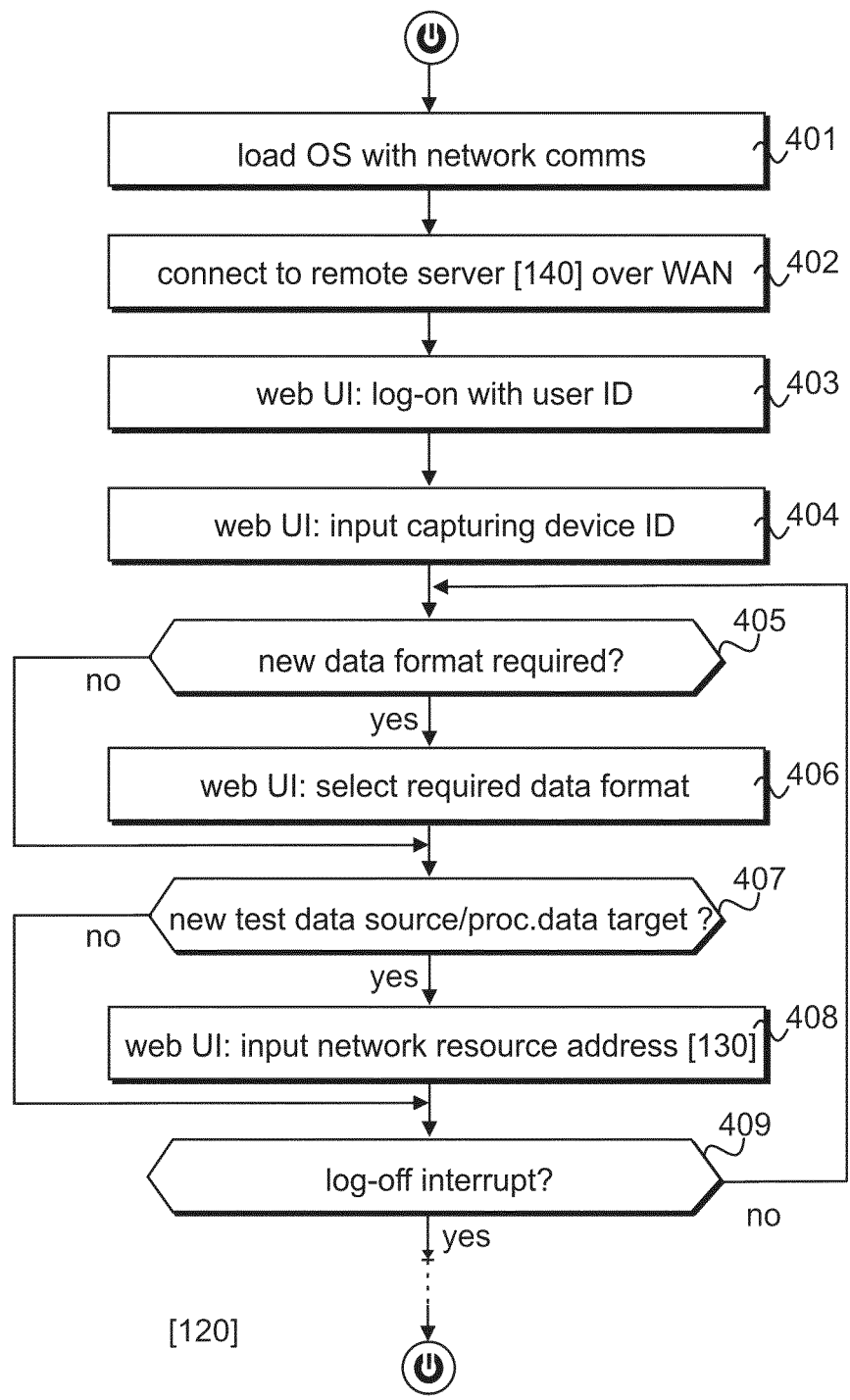
FIG. 4 details steps of a main logic performed at the user terminal shown in FIG. 1 for registering and inputting parameterisation of the networked data capturing device at a remote server.
Figure 5:
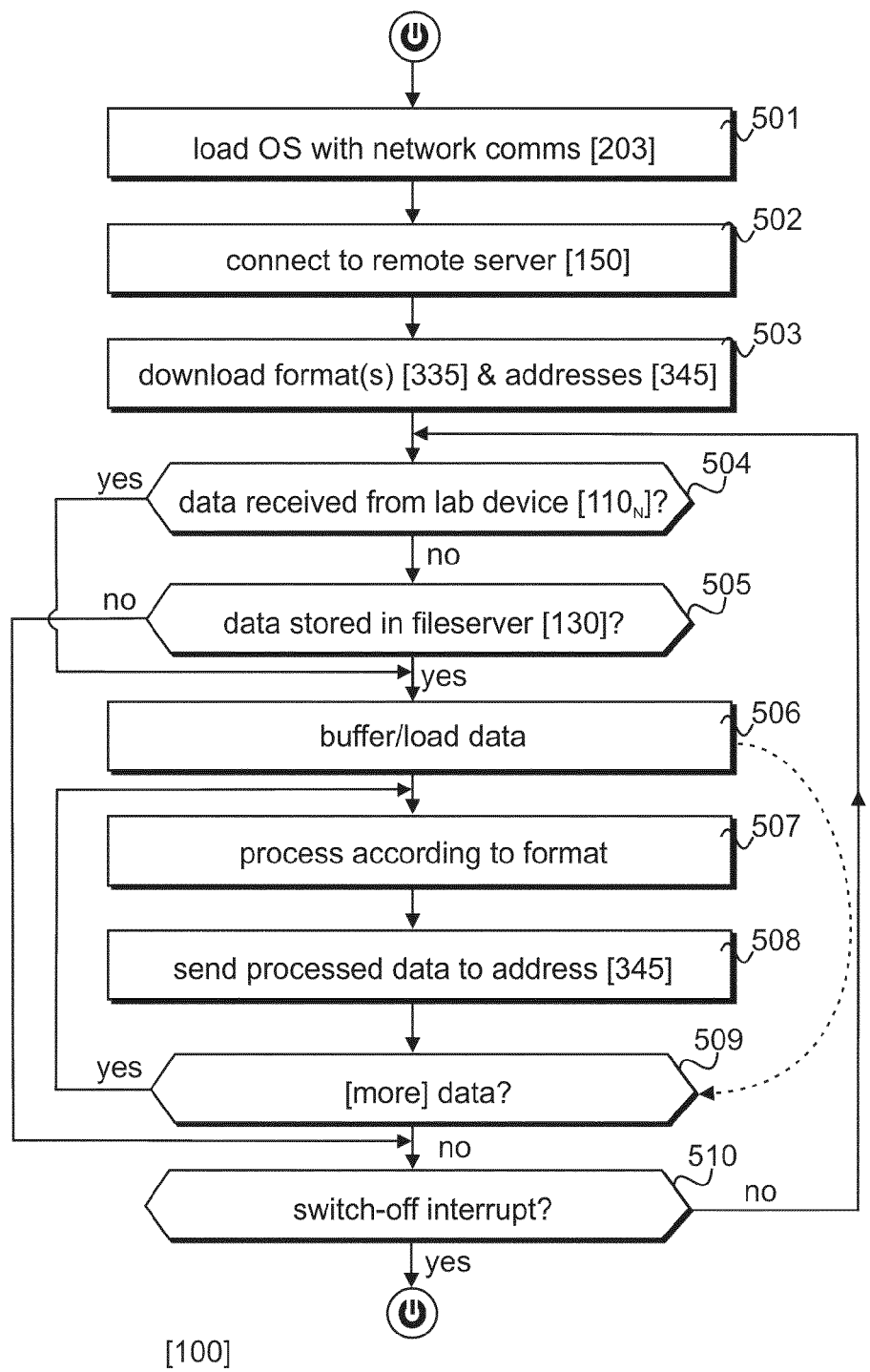
FIG. 5 details steps of the main logic performed by the set of instructions and modules thereof shown in FIG. 3 according to an embodiment of the invention, according to the remote parameterisation of the networked data capturing device shown in FIG. 4.

For the sake of not obscuring the present description unnecessarily, the following assumes an embodiment of the networked data capturing device 100 comprising a CPU 201 associated with a RAM module 202, wherein the contents of the memory means 202 of FIG. 2 during operation of the networked data capturing device 100 are shown in FIG. 3.

An operating system ('OS') is first shown at 301, which may be a variant of Linux® suited to the CPU 201, for instance Archlinux ARM, Ubuntu ARM or mbed OS when the CPU is a Cortex™ chip as previously described, and which includes both instructions for governing the basic data processing, interdependence and interoperability of the device hardware components e.g. as described in FIG. 2; and communication subroutines 302 to configure the capturing device 100 for unilateral (RX) data communication with a connected laboratory equipment device 110 and for bilateral network communication via the NIC 207 interfaced with the wired connection 155 to the local router 155.

A set of instructions is next shown at 310, which is interfaced with the OS 301, particularly the network communication subroutines 302 thereof, via one or more suitable Application Programmer Interfaces ('API') 315, and which configures the capturing device 100 to capture and process test data output by a directly-connected laboratory equipment device, to acquire one or more data files stored at the local fileserver 130 over the LAN and process output test data therein, and to forward the processed data to the remote server 140 across the WAN 160.

Accordingly, the set of instructions 310 firstly comprises a listening-fetching module 320 adapted to listen passively to the output test data streamed by a laboratory equipment device 110$i$ serial port, and to acquire output test data from one or more data files stored at a networked terminal such as the local user terminal 120 or the local fileserver 130. The listening-fetching module 320 comprises a driver sub-module 325 adapted to recognise data type(s), value(s) and format(s) in a data stream output by a connected laboratory equipment device 110$_N$, for instance conforming to the ASTM standard which defines the positions and identifiers used for data nomenclature by the instrument 110, and to extract sampling values, parameters and similar other quantitative data from the test data.

The set of instructions 310 next comprises a translating module 330 adapted to automatically process any extracted test data communicated to it by the driver sub-module 325 into an alternate data stream having a different format defining alternative positions and identifiers. The translating module 330 thus stores data-formatting parameters 335 that are user-predefined at the remote server 140, and is adapted to format the sampling values, parameters and similar other quantitative data in the test data extracted by the driver 325 according to the said predefined parameters.

The set of instructions 310 next comprises a networking module 340 adapted to automatically establish a network session with the remote server 140 across the WAN 160, including through any firewall device, apparatus or construct implemented by the router 150 in the laboratory environment 10, for downloading the predefined data-formatting parameters 335 when the networked data capturing device 100 is first switched on, according to principle described herein. The networking module 340 is further adapted to forward any processed data communicated to it by the formatting module 330, to one or more networked terminals such as the local user terminal 120 and/or the local fileserver 130 across the LAN 155, and/or the remote server 140 across the WAN 160. The networking module 340 thus stores one or more target LAN and/or WAN network addresses 345 that are user-predefined at the remote server 140, besides the WAN network address of the server 140, so that the networking module 340 can correctly address network messages representative of the processed data being transmitted.

Further local and network data 399 may be stored in the memory means 202 of the capturing device 100 at runtime, some or all of which may be processed either by the set of instructions 310, or by or for the OS 301 being processed by the device components in parallel with the set of instructions 310. With reference to FIGS. 4 to 7 described herein, examples of local data include for instance buffered test data 600 captured by the listening-fetching module 320 through the USB or serial I/O interfaces 205, 206 for processing by the driver 325 and translating module 330, buffered file data 600 loaded by the listening-fetching module 320 from the local fileserver 130 for processing by the driver 325 and translating module 330, processed test data 620 for network messaging by the networking module 340, and component device drivers loaded for the invoking by the OS 301. Examples of network data include for instance incoming network messages being received from the local fileserver 130, incoming network messages being received from the remote server 140, outgoing network messages addressed to the remote server 140, and keepalive (KA) network messages being sent by the OS 301 and received from the router 150 and those connected amongst remote terminals 120, 130, 140.

In use, networked data capturing devices 100 of the invention are distributed to users by the administrator of the server 140, each with a unique device identifier such as a serial number or simply the respective media access control ('MAC') address of the NIC 206 therein, and with the set of instructions 310 and at least the network address of the server 140 loaded in the memory 202 or 203, but without any formatting parameter 335 nor further network address(es) 345. After taking delivery of it, a user must first parameterise the networked data capturing device 100 remotely at the remote server 140, and steps of a main logic performed by the user terminal 120 shown in FIG. 1 for registering and inputting parameterisation of the networked data capturing device 100 at the remote server 140 are now described with reference to FIG. 4.

The user terminal 120 is initially switched on, and conventionally loads its operating system, for example Windows 10® manufactured and distributed by the Windows Corporation of Redmond, USA, inclusive of networking subroutines to configure the user terminal 120 for bilateral (TX-RX) data communication with the wired connection 155 to the local router 155 and thence to the remote server 140 across the WAN 160, at step 401. A conventional browser application is next loaded, and directed to a web user interface distributed by the remote server 140 across the WAN 160, at step 402. At step 403, the user of the laboratory terminal 120 inputs authenticating data, such as a unique user identifier, in the web user interface and validly logs on at the remote server 140.

At the next step 404, the user of the laboratory terminal 120 inputs the unique device identifier of the delivered the networked data capturing device 100 in the web user interface, for registering a unique association between the user account corresponding to the authenticating data and the respective unique device identifier of the delivered the networked data capturing device 100 at the remote server 140. After receiving and validating the respective unique device identifier, by checking whether a registration record for the same device identifier is not yet stored, the remote server 140 validates the registration by creating and storing a new registration record with the authenticating data and received unique device identifier, then distributes a formatting selection template to the browser at the user terminal 120.

Figure 6:
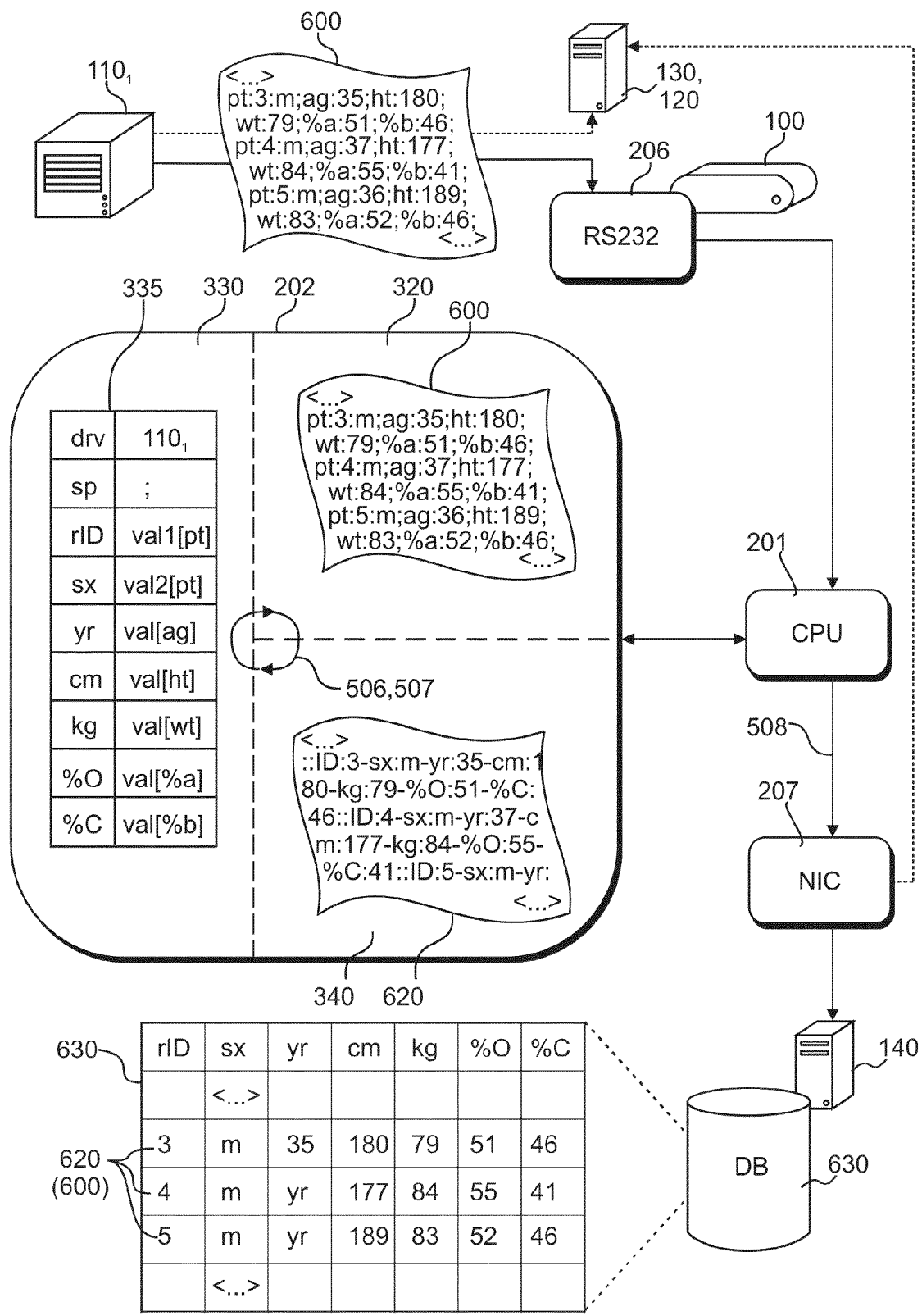
FIG. 6 illustrates a first sub-logic performed by the set of instructions and modules thereof shown in FIGS. 3 and 5, in respect of test data output by a laboratory equipment device in the environment of FIG. 1.
Figure 7:
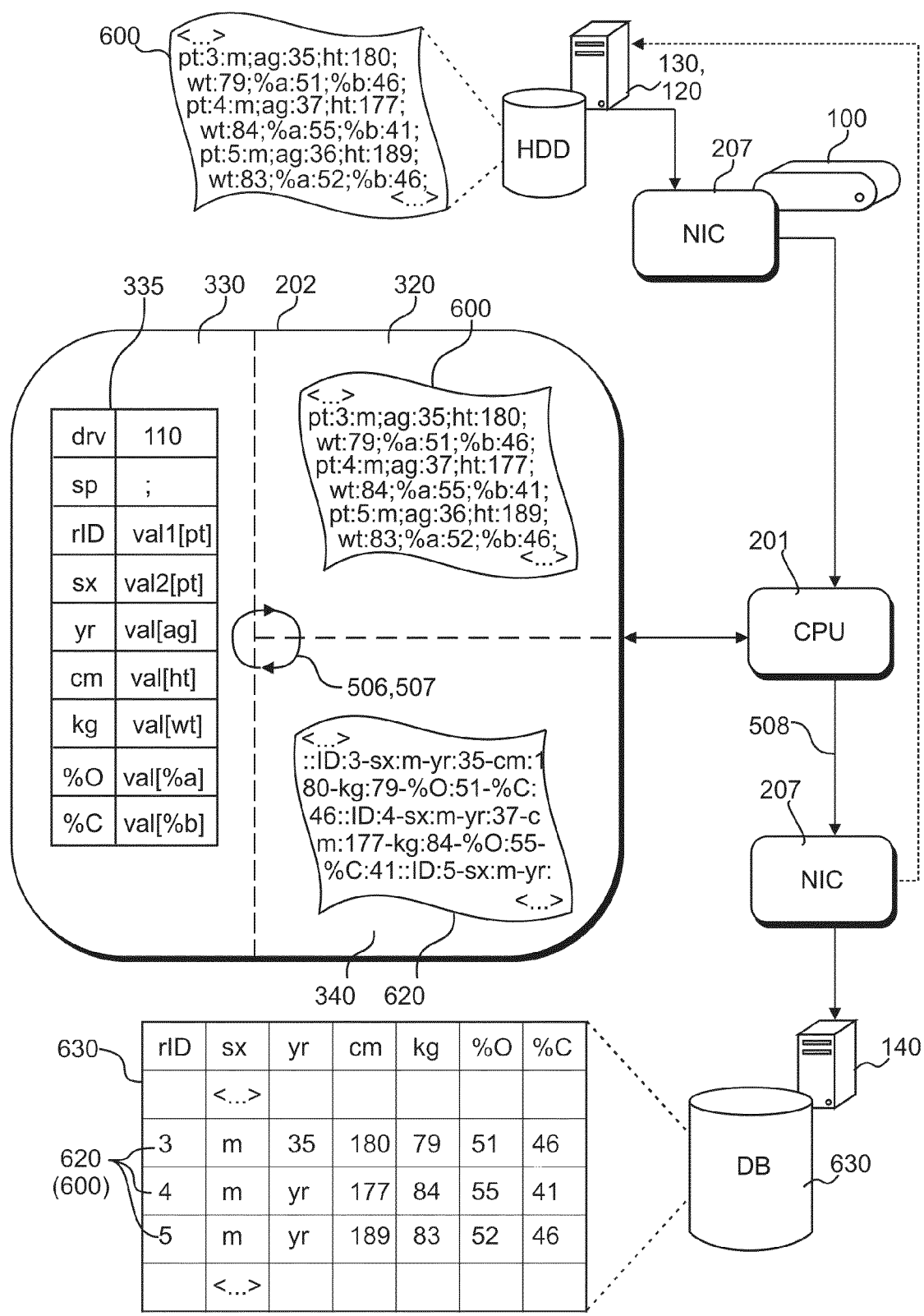
FIG. 7 illustrates a second sub-logic performed by the set of instructions and modules thereof shown in FIGS. 3 and 5, in respect of test data stored at a local fileserver in the environment of FIG. 1.

Accordingly, a first question is asked at step 405, about whether one ore more formatting parameter(s) 335 are required. When the question of step 405 is answered positively, the remote server 140 distributes a formatting selection template to the browser at the user terminal 120, so that the user of the laboratory terminal 120 may associate, or 'map', data type(s), data positions and data identifiers in the ASTM stream of test data output by the instrument 110, with alternative data type(s), data positions and data identifiers desired in the processed data output by the set of instructions 310 and forwarded to remote server(s), for instance an alternative data nomenclature corresponding to field names in a database hosted at any such remote server(s). In one embodiment the activation form will allow the end user to select a driver based on the information provided about the instrument model or the LIS/middleware output file. This can be provided in advance so the driver is already developed and ready for selection by a user. A mapping screen is on the IAMQC Transfer Management Console where the output from the device will be to a predefined format (CSV for example). The mapping screen will allow the end user to input "translations" for data received on the ASTM stream for specified fields/columns that go in the CSV file. Simplified examples of an ASTM stream of test data 600 output by the instrument 110, and of an association with alternative data type(s), data positions and data identifiers by way of illustrating predefined data-formatting parameters 335, are shown in FIGS. 6 and 7.

When the question of step 405 is answered negatively however, a next question is asked at step 407, about whether a new or alternative repository of stored output test data in the LAN 155 and/or the network address of an additional target terminal for the processed test data, should be recorded in the repository 345 at the networked data capturing device 100.

When the question of step 407 is answered positively, then the remote server distributes a networked resource pathway template to the browser at the user terminal 120 so that, at step 408, the user may input in the web user interface, either the network pathway across the LAN 155 corresponding to a shared drive, folder or other structure of the user terminal 120 or the local LIS file server 130, in which any test data directly output to it by the laboratory equipment device 110 is ordinarily stored; and/or the network pathway across the LAN 155 and/or across the WAN, corresponding to a drive, folder or other structure of the user terminal 120, the local LIS file server 130 and/or a further remote server besides remote server 140, to which any test data processed by the capturing device 100 should be automatically sent.

When the question of step 407 is answered negatively however, a question is last asked at step 409, about whether a log off interrupt has been input, for instance an interaction of the user with the graphical user interface of the user terminal OS of the user terminal 120, to close the browser application started at step 402. When the question of step 409 is answered negatively, control returns to the question of step 405, the remote server 140 polling the remote user terminal 120 for any further input or interrupt in a processing loop, until such time as the question of step 409 is eventually answered positively, whereby the session with the remote server 140 is closed, and the user terminal 120 may be used for another purpose and/or switched off eventually.

User inputs and selections defining parameterisation through steps 403 to 408 are received at the remote server 140 and stored in the registration record associated with the respective unique device identifier of the delivered networked data capturing device 100. On a first use of the networked data capturing device 100, steps 405 to 408 correspond to a first basic parameterisation of the new networked data capturing device 100, sufficient to provide basic data processing functionality to the device for capturing output test data from the laboratory equipment device 110, processing it with the application modules 320, 330, 340 and forwarding it to the remote server 140.

Further or alternative parameterisation of the networked data capturing device 100 may be performed at the remote server 140 in a subsequent session, for instance when alternative formatting parameters 335 are required relative to those first entered at registration, and/or when processed test data should be forwarded to a different or additional networked terminal. It will be appreciated that further configuration can be carried out using a Transfer Management Console which can be installed at the laboratory on a PC there. The configuration is then updated to the remote server 140. Steps 402 and 403 are repeated, wherein the initial registration record of step 404 is then identified by the remote server 140 based on the unique association between the user account associated with the logon of step 402 and the respective unique device identifier of the capturing device 100 in the registration record, then steps 405 to 408 are repeated to input the alternative parameterisation and/or LAN/WAN network addresses.

After its physical delivery at the laboratory 10, and an initial registration of the networked data capturing device 100 by performing steps 402 to 408 for that device for the first time, the capturing device 100 is sited, connected to the LAN 155, optionally also connected to the laboratory equipment device 110, then powered up. Steps of the main logic performed by the set of instructions 310 and modules 320, 330, 340 according to the remote parameterisation of steps 402 to 408 are now described with reference to FIGS. 5 to 7, when the capturing device 100 is first powered up.

At step 501, the networked data capturing device 100 loads its operating system 301 inclusive of the networking subroutines 302 and the set of instructions 310. At step 502, the networking module 340 looks up the WAN network address of the remote server 140 in the repository 345 and establishes a network session across the LAN 155 and WAN 160 with the remote server 140. At step 503, the translating module 330 downloads any formatting parameters 335 stored by the remote server 140 as input by the user at step 406, and the networking module 340 downloads any LAN pathway data 345 representative of shared drive(s), folder(s) or other structure(s) of the local user terminal 120 or LIS file server 130, as stored by the remote server 140 after input by the user at step 408. Further to completing the downloading of step 503, the networked data capturing device 100 is fully configured to operate autonomously as described hereafter, until and unless it should be switched off, for relocation, maintenance or another non-data capturing purpose.

A first question is then asked at step 504, corresponding to polling of the USB and serial I/O interfaces 205, 206 by the listening-fetching module 320, about whether there is any output test data 600 being received from a connected laboratory equipment device 110. With reference to FIG. 6, if the question of step 504 is answered positively, then the data stream 600 is captured by the device 100 into a first-in-first-out buffer instantiated in memory 202 at step 506, for processing substantially in real-time by the translating module 330 at step 507 according to the downloaded formatting parameters 335, wherein the size of the buffer corresponds substantially to the processing latency of the device components and overall processing logic of the instructions 310.

If the question of step 504 is answered negatively however, then a next question is asked at step 505 corresponding to, with reference to FIG. 7, querying the shared drive(s), folder(s) or other structure(s) of the user terminal 120 or LIS fileserver 130 through the LAN pathway data 345 by the networking module 340 and the driver 325, about whether there is any new or updated data file of output test data 600 stored at the user terminal 120 or local LIS file server 130. If the question of step 505 is answered positively, then the new or updated data file of output test data 600 is again loaded in memory 202 at step 506, again for processing substantially in real-time at step 507 by the translating module 330 according to the downloaded formatting parameters 335.

Any data 620 processed by the translating module 330 at step 507 is output to the networking module 340 substantially in real-time, which communicates it likewise substantially in real-time to the one or more target(s) networked terminals specified in the repository 145 at step 508, thus any one or more of the user terminal 120 the LIS fileserver 130 and the remote server 140, invariably in the format 335 expected by the target terminal as predefined by the user at step 406.

A question is then asked at step 509, about whether there remains output test data 600 stored either in the FIFO buffer or in the data file loaded from the user terminal 120 or LIS fileserver 130 in the memory 202 to process at step 506. If the question of step 509 is answered positively, control returns to step 507, whereby the output test data from the laboratory equipment device 110 or the LIS fileserver 130 continues to be processed as it is being fetched and buffered/loaded, then communicated to the remote server 140 substantially in real-time, and so on and so forth as represented by a circular dashed arrow in FIGS. 6 and 7.

Alternatively, the question of step 509 is answered negatively and, likewise when the question of step 505 is answered negatively, then control proceeds to a next question at step 510, about whether a switch off interrupt has been received, for instance an interaction of the user with an on/off hardware switch of the networked data capturing device 100. When the question of step 510 is answered negatively, control returns to the initial question of step 504, so that any further output test data being received from a connected laboratory equipment device 110 or new/updated data file at the LIS fileserver 130 may be detected, captured, processed and so on and so forth. Alternatively, the question of step 510 is answered positively, whereby the networked data capturing device 100 is eventually switched off.

Accordingly, the invention disclosed herein provides a set-and-forget data networked capturing device 100 embodying a fully-automated data capturing, processing and distributing methodology for use with laboratory equipment devices and apparatuses, wherein test data 600 output by such laboratory equipment devices and apparatuses is shared quasi-instantaneously, moreover in a compatible data format, with any one or more recipient(s) for their own purposes of analyses and more, whilst dispensing wholly with user interaction or intervention after the initial, remote parameterisation of the device.

In the specification the terms "comprise, comprises, comprised and comprising" or any variation thereof and the terms include, includes, included and including" or any variation thereof are considered to be totally interchangeable and they should all be afforded the widest possible interpretation and vice versa. The invention is not limited to the embodiments hereinbefore described but may be varied in both construction and detail.

The invention claimed is:

1. A networked data capturing device, comprising:
networking means for connecting to one or more remote servers over networks;
at least one local data input interface for connecting to at least one laboratory equipment device;
memory means storing computer executable instructions; and
at least one processor configured to access the memory means and to execute the stored computer executable instructions to
poll the at least one local data input interface for data output by the at least one laboratory equipment device;
automatically obtain output test data representative of testing performed by the laboratory equipment device and formatted according to an application layer protocol wherein the output test data is obtained based upon a polling result, by intercepting a bit stream output by the at least one laboratory equipment device through the at least one local data input interface;
automatically process the obtained data into an alternative format according to a remote parameterisation of the device, wherein the remote parameterisation includes data formatting parameters downloaded by the device from the at least one remote server; and
automatically communicate the processed data to at least one remote server with the networking means,
wherein the networked data capturing device is connected, firstly, to a single serial port of the laboratory equipment device with a serial cable, having a single-side connection engaged with the serial port of the laboratory equipment device, a first of dual-side connector of the serial cable engaged with a matching serial connector of the networked data capturing device, and a second of the dual-side connector engaged with one of: a user terminal or a local laboratory information system (LIS) fileserver, to duplicate data signal output by the laboratory equipment device and permit passive streaming of test data to the networked data capturing device.

2. A networked data capturing device according to claim 1, wherein the at least one processor is configured to execute the stored computer executable instructions to alternatively obtain test data by loading test data from the LIS fileserver.

3. A networked data capturing device according to claim 1, wherein the at least one remote server is one selected from the group comprising a client file server connected to a local area network, a database server connected to a local area network, a database server connected to a wide area network and a web server connected to a wide area network.

4. A networked data capturing device according to claim 1, wherein the obtained test data is formatted according to an application layer protocol compliant with Health Level 7 messaging format and other industry standard messaging formats.

5. A networked data capturing device according to claim 1, wherein the at least one local data input interface comprises a serial data input connector, or a Universal Serial Bus, USB connector, or an 8 position 8 contact, 8P8C, connector.

6. A networked data capturing device according to claim 1, wherein the at least one processor is configured to execute the stored computer executable instructions to capture the output test data into a first-in-first-out buffer instantiated in memory for processing in real-time by a translating module according to downloaded formatting parameters to automatically obtain the test data.

7. A networked data capturing device according to claim 1, wherein the at least one processor is configured to execute the stored computer executable instructions to obtain test data by intercepting a bit stream output by the at least one laboratory equipment device through the at least one local data input interface.

8. A networked data capturing device according to claim 1, wherein the serial cable comprises a Y-shaped splitter serial cable.

9. A system comprising at least one laboratory equipment device having a local data output interface and adapted both to process one or more samples and to output sampling results as the test data through the local data output interface, and at least one networked data capturing device according to claim 1, having its at least one local data input interface connected to the local data output interface, wherein the at least one networked data capturing device comprises:
  networking means for connecting to one or more remote servers over networks;
  at least one local data input interface for connecting to at least one laboratory equipment device;
  memory means storing computer executable instructions; and
  at least one processor configured to access the memory means and to execute the stored computer executable instructions to
  poll the at least one local data input interface for data output by the at least one laboratory equipment device;
  automatically obtain output test data representative of testing performed by the laboratory equipment device and formatted according to an application layer protocol wherein the output test data is obtained based upon a polling result, by intercepting a bit stream output by the at least one laboratory equipment device through the at least one local data input interface;
  automatically process the obtained data into an alternative format according to a remote parameterisation of the device, wherein the remote parameterisation includes data formatting parameters downloaded by the device from the at least one remote server; and
  automatically communicate the processed data to at least one remote server with the networking means,
  wherein the networked data capturing device is connected, firstly, to a single serial port of the laboratory equipment device with a serial cable, having a single-side connection engaged with the serial port of the laboratory equipment device, a first of dual-side connector of the serial cable engaged with a matching serial connector of the networked data capturing device, and a second of the dual-side connector engaged with one of: a user terminal or a local laboratory information system (LIS) fileserver, to duplicate data signal output by the laboratory equipment device and permit passive streaming of test data to the networked data capturing device.

10. A system according to claim 9 wherein, when the at least one laboratory equipment device is connected to a laboratory information system or laboratory information management system through the local data output interface, the connection between the at least one laboratory equipment device and the at least one networked data capturing device comprises a split connection passing test data through to the laboratory information system or laboratory information management system.

11. A system according to claim 9, wherein the remote server hosts a database of test data.

12. A method of distributing test data output by at least one laboratory equipment device, the method comprising the steps of:
  connecting at least one local data input interface of a networked data capturing device according to claim 1 to the at least one laboratory equipment device;
  polling the at least one local data input interface for data output by the at least one laboratory equipment device;
  automatically obtaining the test data, wherein the test data is representative of testing performed by the laboratory equipment device and formatted according to an application layer protocol, wherein the test data is obtained based upon a polling result, by intercepting a bit stream output by the at least one laboratory equipment device through the at least one local data input interface;
  automatically processing the obtained data into an alternative data format according to a remote parameterisation of the device, wherein the remote parameterisation includes data formatting parameters downloaded from the at least one remote server; and
  automatically communicating the processed data to at least one remote server with networking means,
  wherein the networked data capturing device is connected, firstly, to a single serial port of the laboratory equipment device with a serial cable, having a single-side connection engaged with the serial port of the laboratory equipment device, a first of dual-side connector of the serial cable engaged with a matching serial connector of the networked data capturing device, and a second of the dual-side connector engaged with one of: a user terminal or a local laboratory information system (LIS) fileserver, to duplicate data signal output by the laboratory equipment device and permit passive streaming of test data to the networked data capturing device.

13. The method according to claim 12, wherein the step of automatically obtaining comprises the further step of loading test data from a data file stored at a local file server connected to the network.

14. The method according to claim 12, wherein the step of automatically processing the obtained data comprises the further steps of registering the or each networked data capturing device to the at least one remote server inputting and storing parameterisation of the device at the at least one remote server; and downloading the stored parameterisation with the or each networked data capturing device from the at least one remote server.

15. The method according to claim 12, wherein the at least one remote server is one selected from the group comprising a client file server connected to a local area network, a database server connected to a local area network, a database server connected to a wide area network and a web server connected to a wide area network.

16. The method according to claim 15, comprising the further step of loading a set of computer-readable instructions into the networked data capturing device from the database server or the web server over the wide area network for configuring the networked data capturing device to perform the steps of claim 12.

17. The method according to claim 12 wherein the step of automatically obtaining the test data comprises the step of capturing the data into a first-in-first-out buffer instantiated in memory for processing in real-time by a translating module according to downloaded formatting parameters to automatically obtain the test data.

18. The method according to claim 12, wherein the step of automatically processing the obtained data comprises the further steps of:
recognising data type, value and format in the output test data including positions and identifiers used for data nomenclature by the at least one laboratory equipment device; and
generating the processed data having the alternative data format defining alternative positions and identifiers.

19. A non-transitory computer-readable medium storing computer-executable instructions that, when executed by at least one processor, configure the at least one processor to perform operations comprising:
polling a local data input interface connected to a data output interface of at least one laboratory equipment device, for any data output by the at least one laboratory equipment device;
automatically obtaining test data, wherein the test data is representative of testing performed by the laboratory equipment device and formatted according to an application layer protocol;
automatically process the obtained data into an alternative format according to a remote parameterisation of the device, wherein the remote parameterisation includes data formatting parameters downloaded from the at least one remote server; and
automatically communicating the processed data to a remote server with networking means,
wherein the networked data capturing device is connected, firstly, to a single serial port of the laboratory equipment device with a serial cable, having a single-side connection engaged with the serial port of the laboratory equipment device, a first of dual-side connector of the serial cable engaged with a matching serial connector of the networked data capturing device, and a second of the dual-side connector engaged with one of: a user terminal or a local laboratory information system (LIS) fileserver, to duplicate data signal output by the laboratory equipment device and permit passive streaming of test data to the networked data capturing device.

* * * * *